(12) United States Patent
Annis et al.

(10) Patent No.: US 7,622,595 B2
(45) Date of Patent: Nov. 24, 2009

(54) SUBSTITUTED 1H-DIHYDROPYRAZOLES, THEIR PREPARATION AND USE

(75) Inventors: Gary David Annis, Landenberg, PA (US); George Philip Lahm, Wilmington, DE (US); Thomas Paul Selby, Wilmington, DE (US); Thomas Martin Stevenson, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 56 days.

(21) Appl. No.: 11/352,805

(22) Filed: Feb. 13, 2006

(65) Prior Publication Data
US 2006/0128965 A1    Jun. 15, 2006

Related U.S. Application Data

(62) Division of application No. 10/482,556, filed as application No. PCT/US02/25612 on Aug. 13, 2002, now Pat. No. 7,038,057.

(60) Provisional application No. 60/369,659, filed on Apr. 2, 2002, provisional application No. 60/341,894, filed on Dec. 19, 2001, provisional application No. 60/311,919, filed on Aug. 13, 2001.

(51) Int. Cl.
C07D 231/14    (2006.01)
(52) U.S. Cl. .................................. 548/374.1
(58) Field of Classification Search ............... 548/374.1
See application file for complete search history.

(56) References Cited
U.S. PATENT DOCUMENTS
3,153,654 A    10/1964 Ficken
(Continued)

FOREIGN PATENT DOCUMENTS
EP    0 333 131 A    9/1989
(Continued)

OTHER PUBLICATIONS

Donald J.P. Pinto et al., "Discovery of 1-[3-(Aminomethyl)phenyl)-N-[3-fluoro-2'-(methylsulfonyl)-[1,1'-biphenyl]-4-yl]-3-(trifluoromethyl)-1H-pyrazole-5-carboxamide (DPC-423), a Highly Potent, Selective, and Orally Bioavailable inhibitor of Blood Coagulation Factor Xa1", J. Med. Chem., 2001, vol. 44, pp. 566-578.

(Continued)

Primary Examiner—Patricia L Morris

(57) ABSTRACT

This invention provides compounds of Formula I, methods for their preparation and use for preparing compounds of Formula II

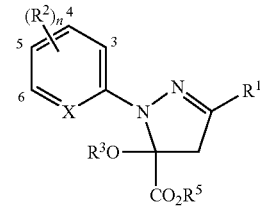

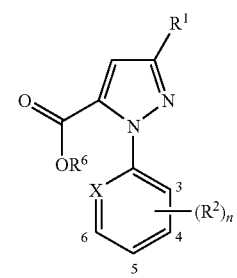

wherein $R^1$, $R^2$, $R^3$, $R^5$, $R^6$, X and n are as defined in the disclosure.

This invention also discloses preparation of compounds of Formula III

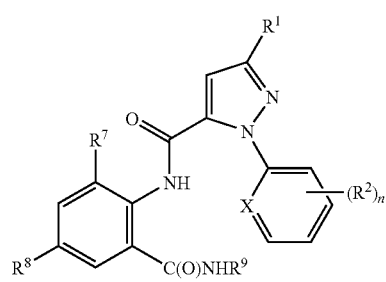

wherein $R^1$, $R^2$, $R^7$, $R^8$, $R^9$ and n are as defined in the disclosure.

This invention also pertains to certain compounds of Formula 4 and 6 used to prepare compounds of Formula I.

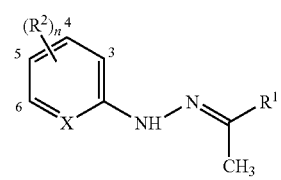

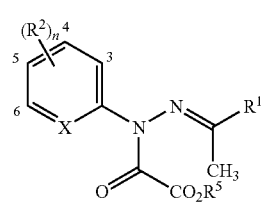

wherein $R^1$, $R^2$, $R^5$, X and n are as defined in the disclosure.

20 Claims, No Drawings

U.S. PATENT DOCUMENTS

| | | | |
|---|---|---|---|
| 5,091,405 A | 2/1992 | Stevenson | |
| 5,945,541 A | 8/1999 | Sohn et al. | |
| 6,747,047 B2 | 6/2004 | Lahm et al. | |
| 6,965,032 B2 | 11/2005 | Freudenberger | |
| 6,995,176 B2 | 2/2006 | Bernotas et al. | |
| 7,015,218 B1 | 3/2006 | Ushio et al. | |
| 2004/0063738 A1* | 4/2004 | Lahm et al. | 514/275 |
| 2004/0110777 A1 | 6/2004 | Annis et al. | |
| 2004/0198984 A1 | 10/2004 | Lahm et al. | |
| 2005/0245560 A1 | 11/2005 | Greenwood et al. | |
| 2005/0282868 A1 | 12/2005 | Finkelstein et al. | |
| 2006/0079561 A1 | 4/2006 | Lahm et al. | |

FOREIGN PATENT DOCUMENTS

| | | |
|---|---|---|
| EP | 1 176 140 B1 | 8/2000 |
| JP | H1-502513 | 8/1989 |
| JP | H1-283274 | 11/1989 |
| NL | 9202078 A | 6/1994 |
| WO | 88/06583 | 9/1988 |
| WO | 02/48137 | 6/2000 |
| WO | 00/47558 | 8/2000 |
| WO | WO 01/70671 | 9/2001 |
| WO | WO 02/48115 | 8/2002 |
| WO | WO 03/015519 | 2/2003 |
| WO | WO 03/016283 | 2/2003 |
| WO | WO 03/016284 | 2/2003 |

OTHER PUBLICATIONS

J. Baumann et al., "Soybean lipoxygenase-1 Inhibition by ketone . . . ", Agents Actions 1992, 12(3), 360-4.

K. H, Pilgram et al. "Selective Instability of trifluoromethyl linked . . . ", J. Heterocycl. Chem. 1988, 25(1), 139-43.

X. J. Liu, "An efficient synthesis of 3-trifluoromethylated . . . ", Synthesis 1999 (8), 1313-1318.

Foti et al., First Synthesis of a Bromonitrilimine. Direct Formation of 3-Bromopyrazole Derivatives, Tetrahedron Letters 40 (1999), pp. 2605-2606.

* cited by examiner

SUBSTITUTED 1H-DIHYDROPYRAZOLES, THEIR PREPARATION AND USE

This application is a division of U.S. application Ser. No. 10/482,556 filed Dec. 30, 2003, now issued as U.S. Pat. No. 7,038,057, which represents a national filing under 35 USC 371 of International Application No. PCT/US02/25612 filed Aug. 13, 2002, claiming priority of U.S. Provisional Application No. 60/369,659 filed Apr. 2, 2002, U.S. Provisional Application No. 60/341,894 filed Dec. 19, 2001 and U.S. Provisional Application No. 60/311,919 filed Aug. 13, 2001.

BACKGROUND OF THE INVENTION

This invention relates to novel carboxylic acid derivatives of 1-aryl-substituted dihydro-1H-pyrazoles and pyrazoles. These compounds are useful for preparation of certain anthranilic amide compounds that are of interest as insecticides (see e.g. PCT Publication WO 01/070671). *J. Med. Chem.* 2001, 44, 566-578 discloses a preparation of 1-(3-cyanophenyl)-3-methyl-1H-pyrazol-5-carboxylic acid and its use in preparing inhibitors of blood coagulation factor Xa. The present invention provides technology useful for the successful and convenient preparation of 1-aryl-substituted dihydro-1H-pyrazoles and pyrazoles.

SUMMARY OF THE INVENTION

This invention provides compounds of Formula I

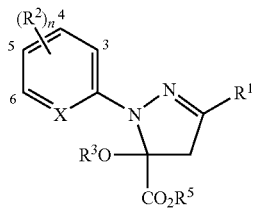

wherein
- $R^1$ is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl or $C_3$-$C_6$ halocycloalkyl;
- each $R^2$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;
- $R^3$ is H, $C_1$-$C_4$ alkyl, $C_2$-$C_4$ alkylcarbonyl or $C_2$-$C_6$ alkoxycarbonyl;
- X is N or $CR^4$;
- $R^4$ is H or $R^2$;
- $R^5$ is $C_1$-$C_4$ alkyl; and
- n is 0 to 3, provided when X is CH then n is at least 1.

This invention further provides a method of preparing a compound of Formula I. This method comprises (1) treating a compound of Formula 6

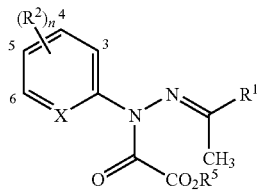

(wherein X, $R^1$, $R^2$, $R^5$ and n are defined as above for Formula I) with a base; and when $R^3$ is $C_1$-$C_4$ alkyl, $C_2$-$C_4$ alkylcarbonyl or $C_2$-$C_6$ alkoxycarbonyl, (2) reacting with an alkylating or acylating agent suitable for substituting an $R^3$ for an alkoxide counterion to form a compound of Formula I.

This invention also provides a compound of Formula 6, as well as a method for preparing a compound of Formula 6. This method comprises treating the compound of Formula 4

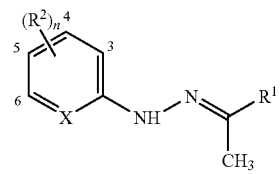

(wherein X, $R^1$, $R^2$ and n are defined as above for Formula I) with a compound of Formula 5

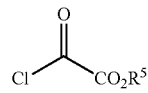

wherein $R^5$ is as defined above for Formula I, in the presence of base to form a compound of Formula 6.

This invention further provides a method of preparing a compound of Formula II

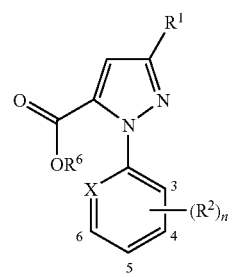

wherein X, $R^1$, $R^2$, and n are defined as above for Formula I, and $R^6$ is $R^5$ as defined above for Formula I or $R^5$ is H. This method comprises (3) treating a compound of Formula I with acid; and when $R^6$ is H (4) converting the product of (3) to form a compound of Formula II wherein $R^6$ is H.

This invention also provides compounds of Formula 4 wherein $R^1$ is $CF_3$; each $R^2$ is independently Cl or Br, and one $R^2$ is at the 3-position; X is N or $CR^4$; $R^4$ is H, Cl or Br; and n is 0, 1, 2 or 3; provided that (i) when X is CH or CCl then n is at least 1 and (ii) when X is CCl, an $R^2$ at the 3-position is Cl and an $R^2$ is at the 5-position is Cl when n is at least 3.

This invention also provides compounds of Formula II wherein $R^1$ is $CF_3$; each $R^2$ is independently Cl or Br, and one $R^2$ is at the 3-position; X is N or $CR^4$; $R^4$ is H or $R^2$; $R^6$ is H or $C_1$-$C_4$ alkyl; and n is 0, 1, 2 or 3, provided when X is CH then n is at least 1.

This invention also involves a method of preparing a compound of Formula III,

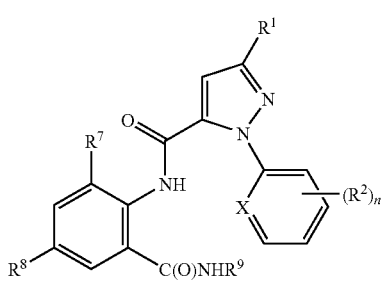

wherein X, $R^1$, $R^2$, and n are defined as above for Formula I; $R^7$ is $CH_3$, Cl or Br; $R^8$ is F, Cl, Br, I or $CF_3$; and $R^9$ is $C_1$-$C_4$ alkyl, using a compound of Formula II wherein $R^6$ is H. This method is characterized by preparing the compound of Formula II by the method as indicated above.

DETAILED DESCRIPTION OF THE INVENTION

In the above recitations, the term "alkyl", used either alone or in compound words such as "alkylthio" or "haloalkyl" includes straight-chain or branched alkyl, such as methyl, ethyl, n-propyl, i-propyl, or the different butyl, pentyl or hexyl isomers. "Alkenyl" can include straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyclobutyl, cyclopentyl and cyclohexyl. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)cycloalkylamino" means a cycloalkylamino group where the hydrogen atom is replaced by an alkyl radical; examples include groups such as (alkyl)cyclopropylamino, (alkyl)cyclobutylamino, (alkyl)cyclopentylamino and (alkyl)cyclohexylamino. Preferably the alkyl in (alkyl)cycloalkylamino is $C_1$-$C_4$ alkyl, while the cycloalkyl in cycloalkylamino and (alkyl)cycloalkylamino is $C_3$-$C_6$ cycloalkyl.

The term "aryl" refers to an aromatic carbocyclic ring or ring system or a heteroaromatic ring or ring system, each ring or ring system optionally substituted. The term "aromatic ring system" denotes fully unsaturated carbocycles and heterocycles in which at least one ring of a polycyclic ring system is aromatic. Aromatic indicates that each of ring atoms is essentially in the same plane and has a p-orbital perpendicular to the ring plane, and in which (4n+2) π electrons, when n is 0 or a positive integer, are associated with the ring to comply with Hückel's rule. The term "aromatic carbocyclic ring system" includes fully aromatic carbocycles and carbocycles in which at least one ring of a polycyclic ring system is aromatic (e. g. phenyl and naphthyl). The term "heteroaromatic ring or ring system" includes fully aromatic heterocycles and heterocycles in which at least one ring of a polycyclic ring system is aromatic and in which at least one ring atom is not carbon and can contain 1 to 4 heteroatoms independently selected from the group consisting of nitrogen, oxygen and sulfur, provided that each heteroaromatic ring contains no more than 4 nitrogens, no more than 2 oxygens and no more than 2 sulfurs (where aromatic indicates that the Hückel rule is satisfied). The heterocyclic ring systems can be attached through any available carbon or nitrogen by replacement of hydrogen on said carbon or nitrogen. More specifically, the term "aryl" refers to the moiety

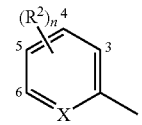

wherein $R^2$, X and n are defined as above and the numerals 3 through 6 indicate respectively the 3-position through the 6-position for substituents on the moiety.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC{\equiv}CCHCl$, $CF_3{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. The terms "alkylaminocarbonyl" and "dialkylaminocarbonyl" include, for example, $CH_3NHC(=O)$, $CH_3CH_2NHC(=O)$ and $(CH_3)_2NC(=O)$.

The total number of carbon atoms in a substituent group is indicated by the "$C_i$-$C_j$" prefix where i and j are numbers from 1 to 8. For example, $C_1$-$C_3$ alkylsulfonyl designates methylsulfonyl through propylsulfonyl. In the above recitations, when a compound of Formula I contains a heteroaromatic ring, all substituents are attached to this ring through any available carbon or nitrogen by replacement of a hydrogen on said carbon or nitrogen.

When a group contains a substituent which can be hydrogen, for example $R^1$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as an optically active form.

Compounds of Formula I and compounds of Formula II can be prepared by the stepwise process comprising:

(a) treating, optionally in the presence of acid, a compound of Formula 2

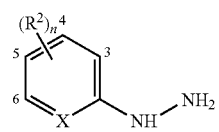

2

(wherein X, $R^2$ and n are defined as above) with a compound of Formula 3

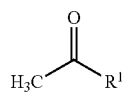

3

(wherein $R^1$ is defined as above) to form a compound of Formula 4

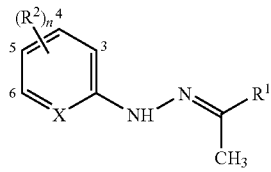

4

(wherein X, $R^1$, $R^2$ and n are defined as above);

(b) treating said compound of Formula 4 with a compound of Formula 5

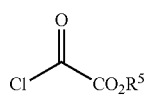

5 wherein $R^5$ is $C_1$-$C_4$ alkyl, in the presence of base to form a compound of Formula 6

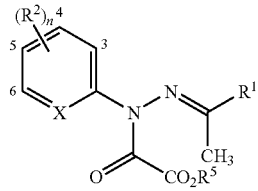

6

(wherein X, $R^1$, $R^2$, $R^5$ and n are defined as above);

(1) treating said compound of Formula 6 with a base to form a compound of Formula I wherein $R^3$ is H; and (2) when $R^3$ is $C_1$-$C_4$ alkyl $C_2$-$C_4$ alkylcarbonyl or $C_2$-$C_6$ alkoxycarbonyl, reacting with an alkylating or acylating agent to form a compound of Formula I

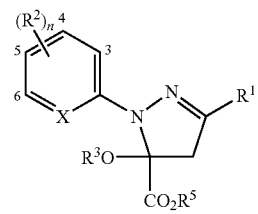

I (wherein X, $R^1$, $R^2$, $R^5$ and n are defined as above);

(3) treating a compound of Formula I with acid; and when $R^6$ is H (4) converting the product of (3) to form a compound of Formula II wherein $R^6$ is H.

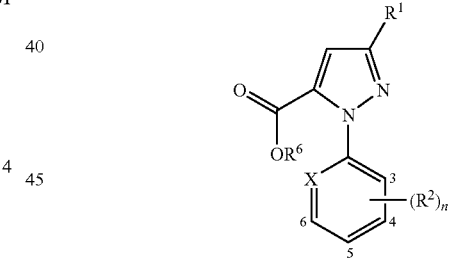

II wherein X, $R^1$, $R^2$, $R^5$ and n are defined as above.

Preferred 1. Compounds of Formula I wherein $R^1$ is H, $C_1$-$C_4$ alkyl or $C_1$-$C_4$ haloalkyl;
  and each $R^2$ is independently $C_1$-$C_4$ alkyl, $C_1$-$C_4$ haloalkyl, halogen or CN.
Preferred 2. Compounds of Formula I wherein
  $R^1$ is H, $C_1$-$C_4$ alkyl or $C_1$-$C_4$ haloalkyl;
  X is N; and
  n is 0.
Preferred 3. Compounds of Preferred 1 wherein
  $R^1$ is $CF_3$;
  each $R^2$ is independently Cl or Br, and one $R^2$ is at the 3-position;
  $R^3$ is H; and
  $R^4$ is H, Cl or Br.

Preferred 4. Compounds of Preferred 1 wherein
$R^1$ is $CF_3$;
one $R^2$ is at the 4-position and is CN, and if an $R^2$ is present at the 5-position, it is F;
$R^3$ is H; and
X is CH.
Preferred 5. Compounds of Preferred 1 wherein X is N.

Of note are the compounds of Formula I (including, but not limited to the compounds of Preferred 1, Preferred 3, Preferred 4 and Preferred 5) wherein n is from 1 to 3.

Preferred 6. The method of preparing a compound of Formula I from a compound of Formula 6 wherein step (1) comprises treating the compound of Formula 6 with a quaternary ammonium fluoride salt.

Preferred 7. The method of preparing a compound of Formula I from a compound of Formula 6 wherein $R^1$ is H, $C_1$-$C_4$ alkyl or $C_1$-$C_4$ haloalkyl; and each $R^2$ is independently $C_1$-$C_4$ alkyl, $C_1$-$C_4$ haloalkyl, halogen or CN.

Preferred 8. The method of Preferred 7 wherein $R^1$ is $CF_3$; and each $R^2$ is independently Cl or Br, and one $R^2$ is at the 3-position.

Preferred 9. The method of Preferred 7 wherein
$R^1$ is $CF_3$;
one $R^2$ is at the 4-position and is CN, and if an $R^2$ is present at the 5-position, it is F;
$R^3$ is H; and
X is CH.

Preferred 10. The method of preparing a compound of Formula I from a compound of Formula 6 wherein X is N.

Of note are methods of preparing a compound of Formula I from a compound of Formula 6 (including, but not limited to the methods of Preferred 6, Preferred 7, Preferred 8, Preferred 9 and Preferred 10) wherein n is from 1 to 3.

Preferred 11. Compounds of Formula 6 wherein $R^1$ is H, $C_1$-$C_4$ alkyl or $C_1$-$C_4$ haloalkyl; and each $R^2$ is independently $C_1$-$C_4$ alkyl, $C_1$-$C_4$ haloalkyl, halogen or CN.

Preferred 12. Compounds of Formula 6 wherein
$R^1$ is H, $C_1$-$C_4$ alkyl or $C_1$-$C_4$ haloalkyl;
X is N; and
n is 0.

Preferred 13. Compounds of Preferred 11 wherein
$R^1$ is $CF_3$;
each $R^2$ is independently Cl or Br, and one $R^2$ is at the 3-position;
X is N or $CR^4$; and
$R^4$ is H, Cl or Br.

Preferred 14. Compounds of Preferred 11 wherein $R^1$ is $CF_3$; one $R^2$ is at the 4-position and is CN, and if an $R^2$ is present at the 5-position, it is F; and X is CH.

Preferred 15. Compounds of Preferred 11 wherein X is N.
Preferred 16. Compounds of Formula II wherein X is N.

Of note are compounds of Formula 6 (including, but not limited to the compounds of Preferred 11, Preferred 13, Preferred 14, and Preferred 15) wherein n is from 1 to 3.

The 3-, 4- or 5-positions are identified by the corresponding numerals shown in the aryl moiety included in Formula I, Formula II, Formula 4 and Formula 6 above.

Of note are compounds of Formula 4 wherein $R^1$ is $CF_3$; each $R^2$ is independently Cl or Br, and one $R^2$ is at the 3-position; X is N or $CR^4$; $R^4$ is H, Cl or Br; and n is 1, 2 or 3.

Of note are compounds of Formula 4 wherein X is N.
Of note are compounds of Formula II wherein n is 1, 2 or 3.
Of note are compounds of Formula II wherein $R^1$ is $CF_3$; each $R^2$ is independently Cl or Br, and one $R^2$ is at the 3-position; X is N or $CR^4$; $R^4$ is H or $R^2$; $R^6$ is H or $C_1$-$C_4$ alkyl; and n is 1, 2 or 3.

Of note are compounds of Formula II wherein when $R^1$ is $CF_3$, n is 1, and $R^2$ selected from Cl or Br is at the 3-position; then X is N. Examples include those where n is from 1 to 3.

Of note are compounds of Formula II wherein when $R^1$ is $CF_3$, n is 1, and $R^2$ selected from Cl or Br is at the 3-position; then X is $CR^4$. Examples include those where n is from 1 to 3.

Preferred methods of preparing compounds I, II and 6 comprise the preferred compounds above.

As shown in Scheme 1, compounds of Formula II can be prepared from compounds of Formula I by treatment with a catalytic amount of a suitable acid. The catalytic acid can be, for example, sulfuric acid. The reaction is generally conducted using an organic solvent. As one skilled in the art will realize, dehydration reactions can be conducted in a wide variety of solvents in a temperature range generally between about 0 and 200° C., more preferably between about 0 and 100° C. For the dehydration in the method of Scheme 1, a solvent comprising acetic acid and temperatures of about 65° C. are preferred. Compounds of Formula I wherein $R^3$ is H are preferred for this transformation. Compounds of Formula II ($R^6$ is $C_1$-$C_4$ alkyl) can be converted to compounds of Formula II ($R^6$ is H) by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). Base-catalyzed hydrolytic methods are preferred. Suitable bases include alkali metal (such as lithium, sodium or potassium) hydroxides. For example, the ester can be dissolved in a mixture of water and alcohol such as ethanol. Upon treatment with sodium hydroxide or potassium hydroxide, the ester is saponified to provide the sodium salt of the carboxylic acid. Acidification with a strong acid, such as hydrochloric acid or sulfuric acid, yields the carboxylic acid. The carboxylic acid can be isolated by methods known to those skilled in the art, including crystallization, extraction and distillation.

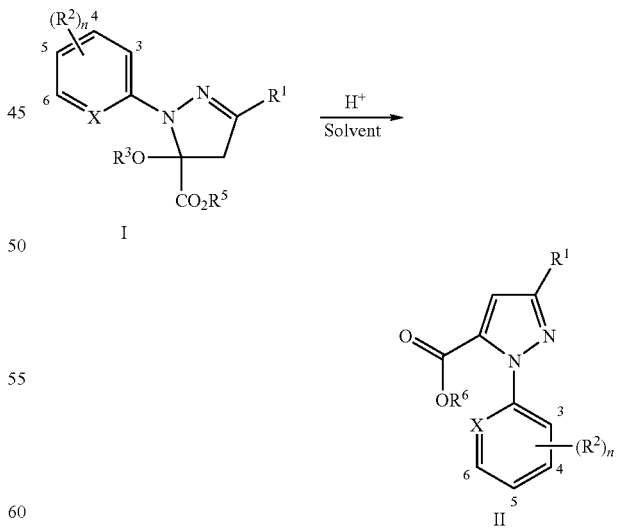

Scheme 1

As illustrated in Scheme 2, compounds of Formula I can be prepared from compounds of Formula 6 by treatment with a suitable base in a suitable organic solvent. Examples of suitable bases include (but are not limited to) sodium hydride, potassium t-butoxide, dimsyl sodium ($CH_3S(O)CH_2^-Na^+$), alkali metal (such as lithium, sodium or potassium) carbonates or hydroxides, tetraalkyl (such as methyl, ethyl or butyl) ammonium fluorides or hydroxides, or 2-tert-butylimino-2-diethylamino-1,3-dimethyl-perhydro-1,3,2-diazaphosphonine. Examples of suitable organic solvents include (but are not limited to) acetone, acetonitrile, tetrahydrofuran, dichloromethane, dimethylsulfoxide, and N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride. The intermediate formed in the reaction, Formula Ia wherein $M^+$ is a suitable counterion derived from the base, is then protonated by a suitable acid (for example, acetic acid) to give compounds of Formula Ib wherein $R^3$ is H. As one skilled in the art will know, intermediates such as Ia may be alkylated or acylated by the addition of a suitable alkylating or acylating agent to give compounds of Formula Ic wherein $R^3$ is $C_1$-$C_4$ alkyl, $C_2$-$C_4$ alkylcarbonyl or $C_2$-$C_6$ alkoxycarbonyl. Alternatively, compounds of Formula Ic can be prepared from compounds of Formula Ib in a separate chemical step using a suitable base and alkylating or acylating agent. Suitable alkylating agents include $C_1$-$C_4$ alkyl halides, sulfates and sulfonates; suitable acylating agents include acid chlorides or anhydrides and chloroformates. In any case, when using Ia or Ib, an alkylating or acylating agent suitable for substituting an $R^3$ for an alkoxide counterion is used.

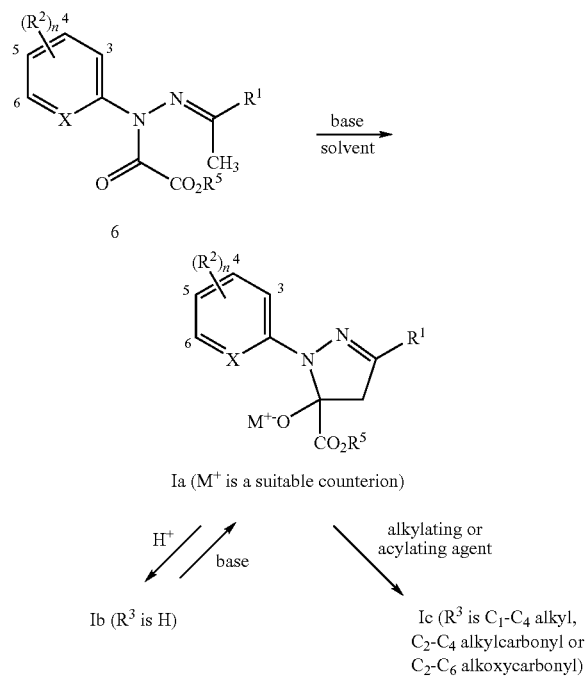

Compounds of Formula 6 can be prepared by treatment of compounds of Formula 4 with compounds of Formula 5 in a suitable organic solvent in the presence of an acid scavenger such as triethylamine. Examples of suitable organic solvents include (but are not limited to) dichloromethane and tetrahydrofuran. The reaction is usually conducted at a temperature between about 0 and 100° C. Scheme 3 illustrates this transformation.

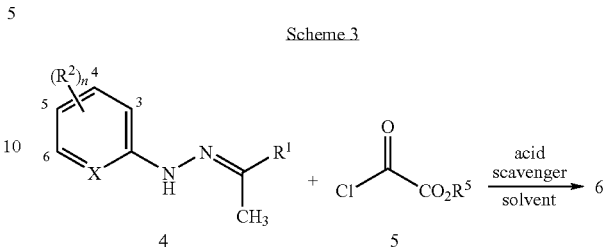

As illustrated by Scheme 4, the hydrazone compound of Formula 4 can be prepared from hydrazine compound of Formula 2 by treatment with a compound of Formula 3 in a solvent such as water, methanol or acetic acid. One skilled in the art will recognize that this reaction may require catalysis by an optional acid and may also require elevated temperatures depending on the molecular substitution pattern of the hydrazone of Formula 4.

Scheme 4

Without further elaboration, it is believed that one skilled in the art using the preceding description can utilize the present invention to its fullest extent. The following Examples are, therefore, to be construed as merely illustrative, and not limiting of the disclosure in any way whatsoever. The starting material for the following Examples may not have necessarily been prepared by a particular preparative run whose procedure is described in other Examples. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

EXAMPLE 1

Preparation of 3-Chloro-2(1H)-pyridinone (2,2,2-trifluoro-1-methylethylidene)hydrazone 1,1,1-Trifluoroacetone (7.80 g, 69.6 mmol) was added to (3-chloro-pyridin-2-yl)-hydrazine (alternatively named (3-chloro-pyridin-2-yl)-hydrazine) (10 g, 69.7 mmol) at 20-25° C. After the addition was complete, the mixture was stirred for about 10 minutes. The solvent was removed under reduced pressure, and the mixture was partitioned between ethyl acetate (100 mL) and saturated sodium carbonate solution (100 mL). The organic layer was dried and evaporated. Chromatography on silica gel (eluted with ethyl acetate) gave the product as an off-white solid (11 g, 66% yield), m.p. 64-64.5° C. (after crystallization from ethyl acetate/hexanes).

IR (nujol) ν 1629, 1590, 1518, 1403, 1365, 1309, 1240, 1196, 1158, 1100, 1032, 992, 800 cm$^{-1}$. $^1$H NMR (CDCl$_3$) δ 2.12 (s, 3H), 6.91-6.86 (m, 1H), 7.6-47.61 (m, 1H), 8.33-8.32 (m, 2H). MS m/z 237 (M$^+$).

EXAMPLE 2

Preparation of Ethyl hydrogen ethanedioate (3-chloro-2-1-pyridinyl) (2,2,2-trifluoro-1-methyl-ethylidene)hydrazide Triethylamine (20.81 g, 0.206 mol) was added to 3-chloro-2(1H)-pyridinone (2,2,2-trifluoro-1-methylethylidene)hydrazone (i.e. the product of Example 1) (32.63 g, 0.137 mol) in dichloromethane (68 mL) at 0° C. Ethyl chlorooxoacetate (18.75 g, 0.137 mol) in dichloromethane (69 mL) was added dropwise to the mixture at 0° C. The mixture was allowed to warm to 25° C. over about 2 hours. The mixture was cooled to 0° C. and a further portion of ethyl chlorooxoacetate (3.75 g, 27.47 mmol) in dichloromethane (14 mL) was added dropwise. After about an additional 1 hour, the mixture was diluted with dichloromethane (about 450 mL), and the mixture was washed with water (2×150 mL). The organic layer was dried and evaporated. Chromatography on silica gel (eluted with 1:1 ethyl acetate-hexanes) gave the product as a solid (42.06 g, 90% yield), m.p. 73.0-73.5° C. (after crystallization from ethyl acetate/hexanes).
IR(nujol) ν 1751, 1720, 1664, 1572, 1417, 1361, 1330, 1202, 1214, 1184, 1137, 1110, 1004, 1043, 1013, 942, 807, 836 cm$^{-1}$. $^1$H NMR (DMSO-d$_6$, 115° C.) δ 1.19 (t, 3H), 1.72 (br s, 3H), 4.25 (q, 2H), 7.65 (dd, J=8.3, 4.7 Hz, 1H), 8.20 (dd, J=7.6, 1.5 Hz, 1H), 8.55 (d, J=3.6 Hz, 1H). MS m/z 337 (M$^+$).

EXAMPLE 3

Preparation of Ethyl 1-(3-chloro-2-pyridinyl)-4,5-dihydro-5-hydroxy-3-(trifluoromethyl)-1H-pyrazole-5-carboxylate Ethyl hydrogen ethanedioate (3-chloro-2-pyridinyl) (2,2,2-trifluoro-1-methyl-ethylidene)hydrazide (i.e. the product of Example 2) (5 g, 14.8 mmol) in dimethyl sulfoxide (25 mL) was added to tetrabutylammonium fluoride hydrate (10 g) in dimethyl sulfoxide (25 mL) over 8 hours. When the addition was complete, the mixture was poured into a mixture of acetic acid (3.25 g) and water (25 mL). After stirring at 25° C. overnight, the mixture was then extracted with toluene (4×25 mL), and the combined toluene extracts were washed with water (50 mL), dried and evaporated to give a solid. Chromatography on silica gel (eluted with 1:2 ethyl acetate-hexanes) gave the product as a solid (2.91 g, 50% yield, containing about 5% of 3-chloro-2(1H)-pyridinone (2,2,2-trifluoro-1-methylethylidene)hydrazone), m.p. 78-78.5° C. (after recrystallization from ethyl acetate/hexanes).
IR (nujol) ν 3403, 1726, 1618, 1582, 1407, 1320, 1293, 1260, 1217, 1187, 1150, 1122, 1100, 1067, 1013, 873, 829 cm$^{-1}$. $^1$H NMR (CDCl$_3$) δ 1.19 (s, 3H), 3.20 (½ of ABZ pattern, J=18 Hz, 1H), 3.42 (½ of ABZ pattern, J=18 Hz, 1H), 4.24 (q, 2H), 6.94 (dd, J=7.9, 4.9 Hz, 1H), 7.74 (dd, J=7.7, 1.5 Hz, 1H), 8.03 (dd, J=4.7, 1.5 Hz, 1H). MS m/z 319 (M$^+$).

EXAMPLE 4

Preparation of Ethyl 1-(3-chloro-2-pyridinyl)-3-(triflouromethyl)-1H-pyrazole-5-carboxylate Sulfuric acid (concentrated, 2 drops) was added to ethyl 1-(3-chloro-2-pyridinyl)-4,5-dihydro-5-hydroxy-3-(trifluoromethyl)-1H-pyrazole-5-carboxylate (i.e. the product of Example 3) (1 g, 2.96 mmol) in acetic acid (10 mL) and the mixture was warmed to 65° C. for about 1 hour. The mixture was allowed to cool to 25° C. and most of the acetic acid was removed under reduced pressure. The mixture was partitioned between saturated aqueous sodium carbonate solution (100 mL) and ethyl acetate (100 mL). The aqueous layer was further extracted with ethyl acetate (100 mL). The combined organic extracts were dried and evaporated to give the product as an oil (0.66 g, 77% yield).
IR (neat) ν 3147, 2986, 1734, 1577, 1547, 1466, 1420, 1367, 1277, 1236, 1135, 1082, 1031, 973, 842, 802 cm$^{-1}$. $^1$H NMR (CDCl$_3$) δ 1.23 (t, 3H), 4.25 (q, 2H), 7.21 (s, 1H), 7.48 (dd, J=8.1, 4.7 Hz, 1H), 7.94 (dd, J=6.6, 2 Hz, 1H), 8.53 (dd, J=4.7, 1.5 Hz, 1H). MS m/z 319 (M$^+$).

EXAMPLE 5

Preparation of 1-(3-chloro-2-pyridinyl)-3-(trifluoromethyl)-1H-pyrazole-5-carboxylic acid Potassium hydroxide (0.5 g, 85%, 2.28 mmol) in water (1 mL) was added to ethyl 1-(3-chloro-2-pyridinyl)-3-(trifluoromethyl)-1H-pyrazole-5-carboxylate (i.e. the product of Example 4) (0.66 g, 2.07 mmol) in ethanol (3 mL). After about 30 minutes, the solvent was removed under reduced pressure, and the mixture was dissolved in water (40 mL). The solution was washed with ethyl acetate (20 mL). The aqueous layer was acidified with. concentrated hydrochloric acid and was extracted with ethyl acetate (3×20 mL). The combined extracts were dried and evaporated to give the product as a solid (0.53 g, 93% yield), m.p. 178-179° C. (after crystallization from hexanes-ethyl acetate).
IR (nujol) ν 1711, 1586, 1565, 1550, 1440, 1425, 1292, 1247, 1219, 1170, 1135, 1087, 1059, 1031, 972, 843, 816 cm$^{-1}$. $^1$H NMR (DMSO-d$_6$) δ 7.61 (s, 1H), 7.77 (m, 1H), 8.30 (d, 1H), 8.60 (s, 1H).

By the procedures described herein together with methods known in the art, the following compounds of Tables 1 to 5 can be prepared. The following abbreviations are used in the Tables: t is tertiary, s is secondary, n is normal, i is iso, Me is methyl, Et is ethyl, Pr is propyl, i-Pr is isopropyl and t-Bu is tertiary butyl.

TABLE 1

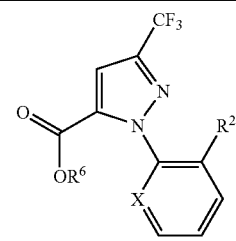

| X is N | | X is CH | | | | | |
|---|---|---|---|---|---|---|---|
| R$^2$ | R$^6$ | R$^2$ | R$^6$ | R$^2$ | R$^6$ | R$^2$ | R$^6$ |
| Cl | H | Br | H | Cl | H | Br | H |
| Cl | Me | Br | Me | Cl | Me | Br | Me |
| Cl | Et | Br | Et | Cl | Et | Br | Et |
| Cl | n-Pr | Br | n-Pr | Cl | n-Pr | Br | n-Pr |
| Cl | i-Pr | Br | i-Pr | Cl | i-Pr | Br | i-Pr |
| Cl | n-Bu | Br | n-Bu | Cl | n-Bu | Br | n-Bu |
| Cl | i-Bu | Br | i-Bu | Cl | i-Bu | Br | i-Bu |

TABLE 1-continued

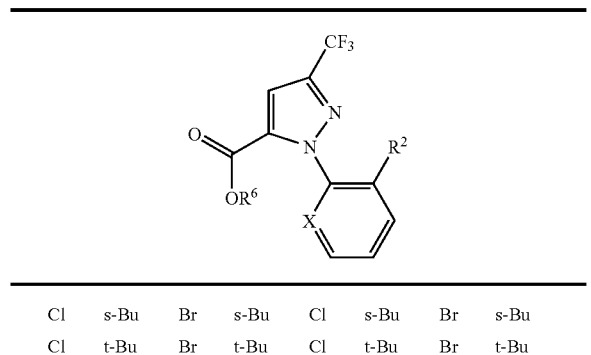

| R² | R⁶ | R² | R⁶ | R² | R⁶ | R² | R⁶ |
|---|---|---|---|---|---|---|---|
| Cl | s-Bu | Br | s-Bu | Cl | s-Bu | Br | s-Bu |
| Cl | t-Bu | Br | t-Bu | Cl | t-Bu | Br | t-Bu |

| X is CCl | | X is CBr | |
|---|---|---|---|
| R² | R⁶ | R² | R⁶ | R² | R⁶ | R² | R⁶ |
| Cl | H | Br | H | Cl | H | Br | H |
| Cl | Me | Br | Me | Cl | Me | Br | Me |
| Cl | Et | Br | Et | Cl | Et | Br | Et |
| Cl | n-Pr | Br | n-Pr | Cl | n-Pr | Br | n-Pr |
| Cl | i-Pr | Br | i-Pr | Cl | i-Pr | Br | i-Pr |
| Cl | n-Bu | Br | n-Bu | Cl | n-Bu | Br | n-Bu |
| Cl | i-Bu | Br | i-Bu | Cl | i-Bu | Br | i-Bu |
| Cl | s-Bu | Br | s-Bu | Cl | s-Bu | Br | s-Bu |
| Cl | t-Bu | Br | t-Bu | Cl | t-Bu | Br | t-Bu |

TABLE 2

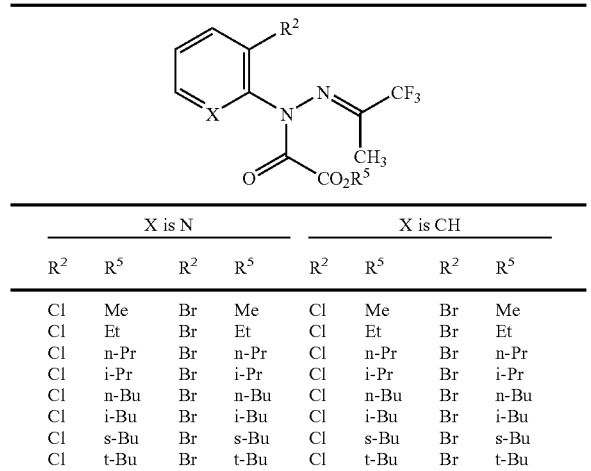

| X is N | | X is CH | |
|---|---|---|---|
| R² | R⁵ | R² | R⁵ | R² | R⁵ | R² | R⁵ |
| Cl | Me | Br | Me | Cl | Me | Br | Me |
| Cl | Et | Br | Et | Cl | Et | Br | Et |
| Cl | n-Pr | Br | n-Pr | Cl | n-Pr | Br | n-Pr |
| Cl | i-Pr | Br | i-Pr | Cl | i-Pr | Br | i-Pr |
| Cl | n-Bu | Br | n-Bu | Cl | n-Bu | Br | n-Bu |
| Cl | i-Bu | Br | i-Bu | Cl | i-Bu | Br | i-Bu |
| Cl | s-Bu | Br | s-Bu | Cl | s-Bu | Br | s-Bu |
| Cl | t-Bu | Br | t-Bu | Cl | t-Bu | Br | t-Bu |

| X is CCl | | X is CBr | |
|---|---|---|---|
| R² | R⁵ | R² | R⁵ | R² | R⁵ | R² | R⁵ |
| Cl | Me | Br | Me | Cl | Me | Br | Me |
| Cl | Et | Br | Et | Cl | Et | Br | Et |
| Cl | n-Pr | Br | n-Pr | Cl | n-Pr | Br | n-Pr |
| Cl | i-Pr | Br | i-Pr | Cl | i-Pr | Br | i-Pr |
| Cl | n-Bu | Br | n-Bu | Cl | n-Bu | Br | n-Bu |
| Cl | i-Bu | Br | i-Bu | Cl | i-Bu | Br | i-Bu |
| Cl | s-Bu | Br | s-Bu | Cl | s-Bu | Br | s-Bu |
| Cl | t-Bu | Br | t-Bu | Cl | t-Bu | Br | t-Bu |

TABLE 3

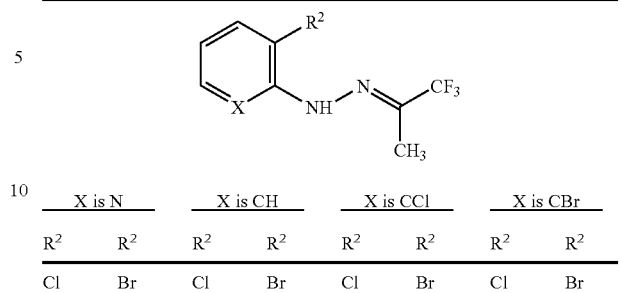

| X is N | X is CH | X is CCl | X is CBr |
|---|---|---|---|
| R² | R² | R² | R² | R² | R² | R² | R² |
| Cl | Br | Cl | Br | Cl | Br | Cl | Br |

TABLE 4

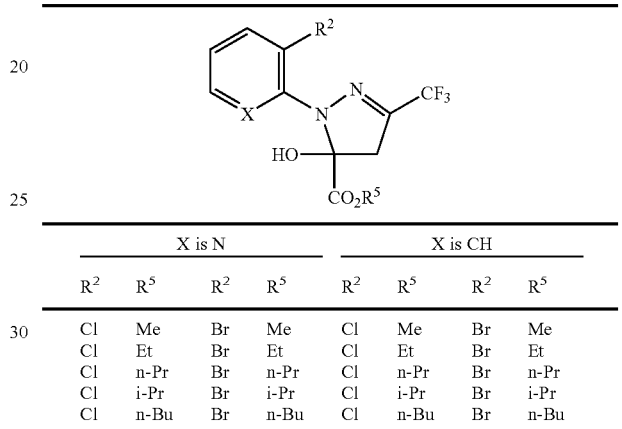

| X is N | | X is CH | |
|---|---|---|---|
| R² | R⁵ | R² | R⁵ | R² | R⁵ | R² | R⁵ |
| Cl | Me | Br | Me | Cl | Me | Br | Me |
| Cl | Et | Br | Et | Cl | Et | Br | Et |
| Cl | n-Pr | Br | n-Pr | Cl | n-Pr | Br | n-Pr |
| Cl | i-Pr | Br | i-Pr | Cl | i-Pr | Br | i-Pr |
| Cl | n-Bu | Br | n-Bu | Cl | n-Bu | Br | n-Bu |
| Cl | i-Bu | Br | i-Bu | Cl | i-Bu | Br | i-Bu |
| Cl | s-Bu | Br | s-Bu | Cl | s-Bu | Br | s-Bu |
| Cl | t-Bu | Br | t-Bu | Cl | t-Bu | Br | t-Bu |

| X is CCl | | X is CBr | |
|---|---|---|---|
| R² | R⁵ | R² | R⁵ | R² | R⁵ | R² | R⁵ |
| Cl | Me | Br | Me | Cl | Me | Br | Me |
| Cl | Et | Br | Et | Cl | Et | Br | Et |
| Cl | n-Pr | Br | n-Pr | Cl | n-Pr | Br | n-Pr |
| Cl | i-Pr | Br | i-Pr | Cl | i-Pr | Br | i-Pr |
| Cl | n-Bu | Br | n-Bu | Cl | n-Bu | Br | n-Bu |
| Cl | i-Bu | Br | i-Bu | Cl | i-Bu | Br | i-Bu |
| Cl | s-Bu | Br | s-Bu | Cl | s-Bu | Br | s-Bu |
| Cl | t-Bu | Br | t-Bu | Cl | t-Bu | Br | t-Bu |

TABLE 5

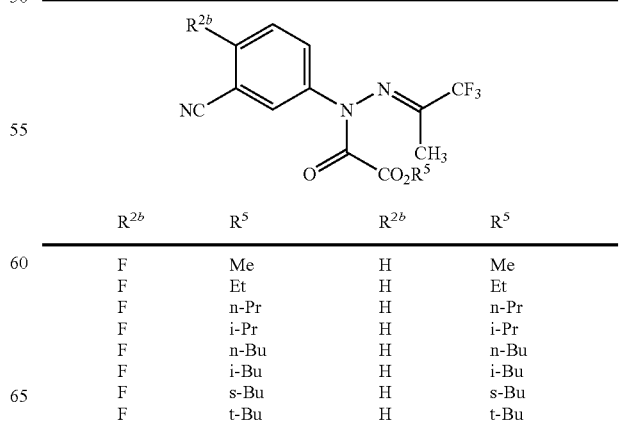

| R²ᵇ | R⁵ | R²ᵇ | R⁵ |
|---|---|---|---|
| F | Me | H | Me |
| F | Et | H | Et |
| F | n-Pr | H | n-Pr |
| F | i-Pr | H | i-Pr |
| F | n-Bu | H | n-Bu |
| F | i-Bu | H | i-Bu |
| F | s-Bu | H | s-Bu |
| F | t-Bu | H | t-Bu |

TABLE 5-continued

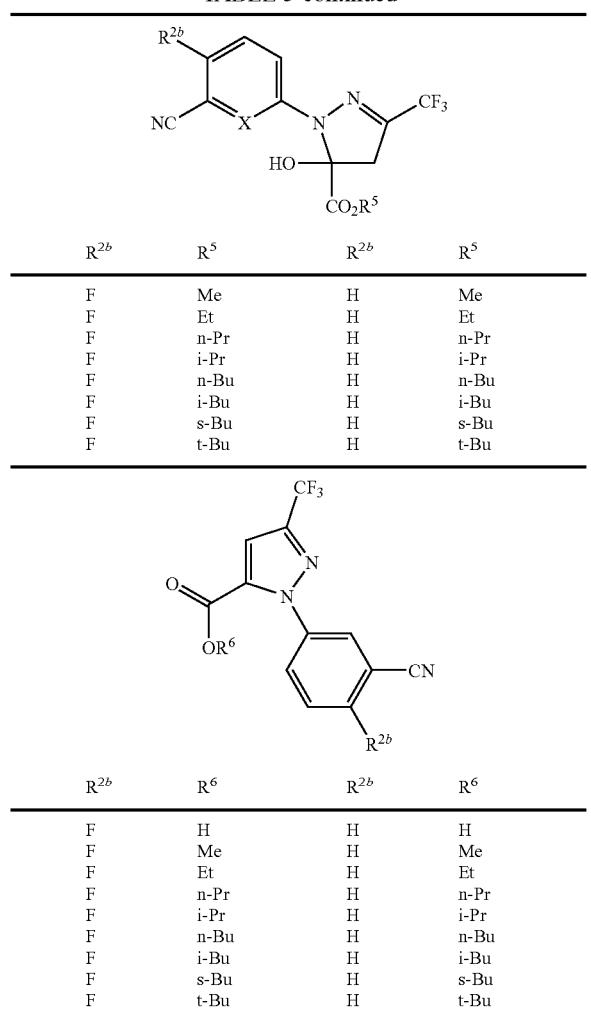

| $R^{2b}$ | $R^5$ | $R^{2b}$ | $R^5$ |
|---|---|---|---|
| F | Me | H | Me |
| F | Et | H | Et |
| F | n-Pr | H | n-Pr |
| F | i-Pr | H | i-Pr |
| F | n-Bu | H | n-Bu |
| F | i-Bu | H | i-Bu |
| F | s-Bu | H | s-Bu |
| F | t-Bu | H | t-Bu |

| $R^{2b}$ | $R^6$ | $R^{2b}$ | $R^6$ |
|---|---|---|---|
| F | H | H | H |
| F | Me | H | Me |
| F | Et | H | Et |
| F | n-Pr | H | n-Pr |
| F | i-Pr | H | i-Pr |
| F | n-Bu | H | n-Bu |
| F | i-Bu | H | i-Bu |
| F | s-Bu | H | s-Bu |
| F | t-Bu | H | t-Bu |

Utility

The compounds of Formulae I, II, 4 and 6 are useful as synthetic intermediates for preparing a compound of Formula III

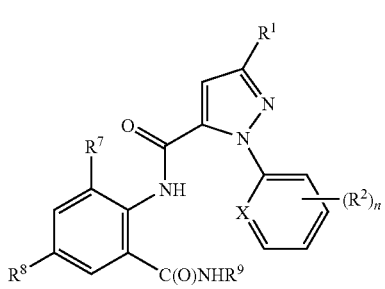

III wherein X, $R^1$, $R^2$ and n are defined as above; $R^7$ is $CH_3$, Cl or Br; $R^8$ is F, Cl, Br, I or $CF_3$; and $R^9$ is $C_1$-$C_4$ alkyl.

Compounds of Formula III are useful as insecticides.

Compounds of Formula III can be prepared from compounds of Formula II (and in turn from compounds of Formula 4, 6 and I) by the processes outlined in Schemes 5-7.

Coupling of a pyrazolecarboxylic acid of Formula IIa (a compound of Formula II wherein $R^6$ is H) with an anthranilic acid of Formula 7 provides a benzoxazinone of Formula 8. In Scheme 5, a benzoxazinone of Formula 8 is prepared directly via sequential addition of methanesulfonyl chloride in the presence of a tertiary amine such as triethylamine or pyridine to a pyrazolecarboxylic acid of Formula IIa, followed by the addition of an anthranilic acid of Formula 7, followed by a second addition of tertiary amine and methanesulfonyl chloride. This procedure generally affords good yields of the benzoxazinone.

Scheme 5

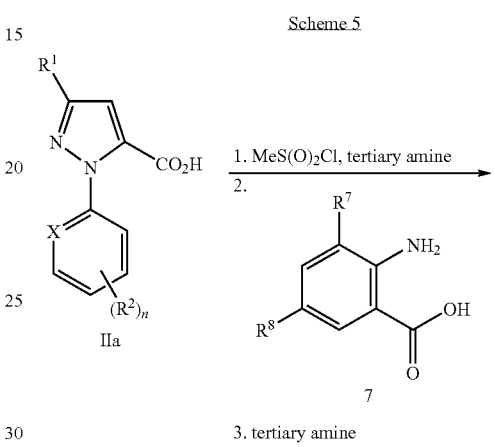

3. tertiary amine
4. MeS(O)$_2$Cl

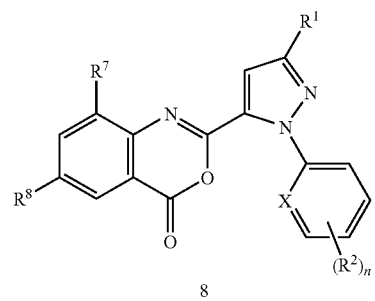

8

Scheme 6 depicts an alternate preparation of benzoxazinones of Formula 8 involving coupling of a pyrazole acid chloride of Formula 10 with an isatoic anhydride of Formula 9 to provide the Formula 8 benzoxazinone directly.

Scheme 6

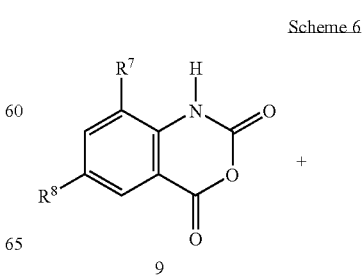

9

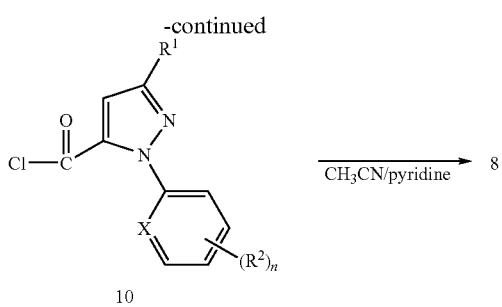

Solvents such as pyridine or pyridine/acetonitrile are suitable for this reaction. The acid chlorides of Formula 10 are available from the corresponding acids of Formula IIa by known procedures such as chlorination with thionyl chloride or oxalyl chloride.

Compounds of Formula III can be prepared by the reaction of benzoxazinones of Formula 8 with $C_1$-$C_4$ alkyl amines as outlined in Scheme 7. The reaction can be run neat or in a variety of suitable solvents including tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095-2103 and references cited within. See also Coppola, *J. Heterocyclic Chemistry* 1999, 36, 563-588.

Scheme 7

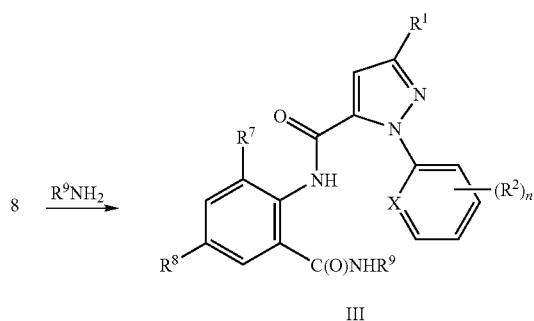

Of note are methods of preparing compounds of Formula III wherein n is 0.

Also of note are methods of preparing compounds of Formula III wherein n is from 1 to 3.

What is claimed is:

1. A compound of Formula II

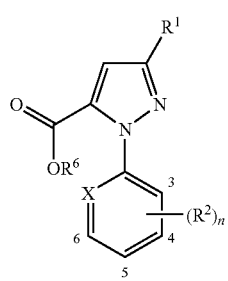

wherein $R^1$ is $CF_3$; each $R^2$ is independently Cl or Br, and one $R^2$ is at the 3-position; X is $CR^4$; $R^4$ is H, Cl or Br; $R^6$ is H or $C_1$ to $C_4$ alkyl; and n is 0 to 3, provided when X is CH then n is at least 1.

2. A compound of claim 1 wherein n is 1 to 3.

3. A compound of claim 1 which is 1-(1-chloro-2-phenyl)-3-(trifluoromethyl)-1H-pyrazole-5-carboxylic acid.

4. A compound of claim 1 which is methyl 1-(1-chloro-2-phenyl)-3-(tifluoromethyl)-1H-pyrazole-5-carboxylate.

5. A compound of claim 1 which is ethyl 1-(1-chloro-2-phenyl)-3-(trifluoromethyl)-1H-pyrazole-5-carboxylate.

6. A method of preparing a compound of Formula II of claim 1, comprising (3) treating a compound of Formula I

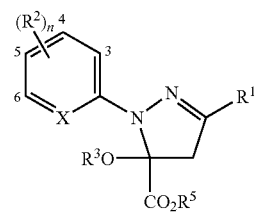

wherein $R^3$ is H, $C_1$-$C_4$ alkyl, $C_2$-$C_4$ alkylcarbonyl or $C_2$-$C_6$ alkoxycarbonyl; and $R^5$ is $C_1$-$C_4$ alkyl, with acid; and when $R^6$ is H, (4) converting the product of (3) to form a compound of Formula II wherein $R^6$ is H.

7. A method of preparing the compound of claim 3, comprising treating a compound selected from the group consisting of methyl 1-(1-chloro-2-phenyl)-4,5-dihydro-5-hydroxy-3-(trifluoromethyl)-1H-pyrazole-5-carboxylate and ethyl 1-(1-chloro-2-phenyl)-4,5-dihydro-5-hydroxy-3-(trifluoromethyl)-1H-pyrazole-5-carboxylate with sulfuric acid; hydrolyzing the product of said treatment using potassium hydroxide; and acidifying the hydrolyzed product with hydrochloric acid.

8. A method of preparing the compound of claim 4, comprising treating methyl 1-(1-chloro-2-phenyl)-4,5-dihydro-5-hydroxy-3-(trifluoromethyl)-1H-pyrazole-5-carboxylate with sulfuric acid.

9. A method of preparing the compound of claim 5, comprising treating ethyl 1-(1-chloro-2-phenyl)-4,5-dihydro-5-hydroxy-3-(trifluoromethyl)-1H-pyrazole-5-carboxylate with sulfuric acid.

10. The method of claim 6 wherein the compound of Formula I is prepared using a method comprising (1) treating a compound of Formula 6

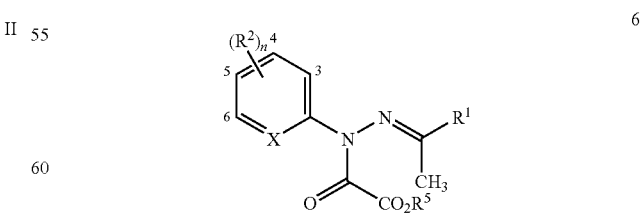

with a base; and when $R^3$ is $C_1$-$C_4$ alkyl, $C_2$-$C_4$ alkylcarbonyl or $C_2$-$C_6$ alkoxycarbonyl, (2) reacting with an alkylating or acylating agent suitable for substituting an $R^3$ for an alkoxide counterion.

11. The method of claim 10 wherein step (1) comprises treating the compound of Formula 6 with a quaternary ammonium fluoride salt.

12. The method of claim 10 wherein the compound of Formula 6 is prepared using a method comprising treating in the presence of base a compound of Formula 4

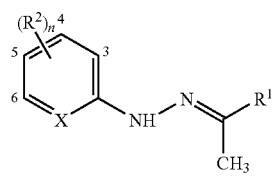

with a compound of Formula 5

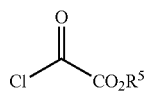

wherein $R^5$ is $C_1$-$C_4$ alkyl.

13. A method of preparing a compound of Formula II of claim 1, comprising
  (3) treating a compound of Formula I

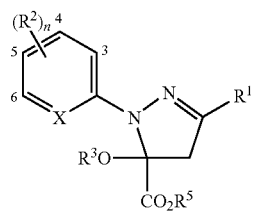

wherein $R^3$ is H, $C_1$-$C_4$ alkyl, $C_2$-$C_4$ alkylcarbonyl or $C_2$-$C_6$ alkoxycarbonyl; and $R^5$ is $C_1$-$C_4$ alkyl, with acid; and when $R^6$ is H,
  (4) hydrolyzing and acidifying the product of (3) to form a compound of Formula II wherein $R^6$ is H.

14. A method of preparing the compound of claim 3, comprising treating a compound selected from the group consisting of methyl 1-(1-chloro-2-phenyl)-4,5-dihydro-5-hydroxy-3-(trifluoromethyl)-1H-pyrazole-5-carboxylate and ethyl 1-(1-choloro-2-phenyl)-4,5-dihydro-5-hydroxy-3-(trifluoromethyl)-1H-pyrazole-5-carboxylate with sulfuric acid in an organic solvent; hydrolyzing the product of said treatment using potassium hydroxide; and acidifying the hydrolyzed product with hydrochloric acid.

15. The method of claim 6 wherein in step (3) the compound of Formula I is treated with an acid in an organic solvent.

16. The method of claim 6 wherein in step (3) the compound of Formula I is treated with an acid in an organic solvent at a temperature within the range between about 0° C. and 200° C. to prepare a compound of Formula II wherein $R^6$ is $C_1$-$C_4$; and when preparing a compound of Formula II wherein $R^6$ is H, the compound of step (3) is hydrolyzed in a mixture of water and alcohol using an alkali metal base and the hydrolyzed compound is reacted with an acid to provide a compound of Formula II wherein $R^6$ is H.

17. A method of preparing the compound of claim 4 comprising treating methyl 1-(1-chloro-2-phenyl)-4,5-dihydro-5-hydroxy-3-(trifluoromethyl)-1H-pyrazole-5-carboxylate with sulfuric acid in an organic solvent at a temperature within the range between about 0° C. and 200° C. to prepare methyl 1-(1-chloro-2-phenyl)-3-(trifluoromethyl)-1H-pyrazole-5-carboxylate.

18. A method of preparing the compound of claim 5 comprising treating ethyl 1-(1-chloro-2-phenyl)-4,5-dihydro-5-hydroxy-3-(trifluoromethyl)-1H-pyrazole-5-carboxylate with sulfuric acid in an organic solvent at a temperature within the range between about 0° C. and 200° C. to prepare ethyl 1-(1-chloro-2-phenyl)-3-(trifluoromethyl)-1H-pyrazole-5-carboxylate.

19. A process for preparing a compound of Formula II of claim 1, comprising
  (A) preparing a compound of Formula I

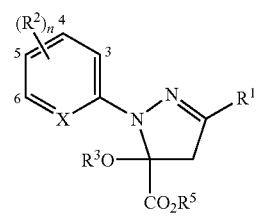

wherein $R^3$ is H, $C_1$-$C_4$ alkyl, $C_2$-$C_4$ alkylcarbonyl or $C_2$-$C_6$ alkoxycarbonyl; and $R^5$ is $C_1$-$C_4$ alkyl; by a method comprising
  (1) treating a compound of Formula 6

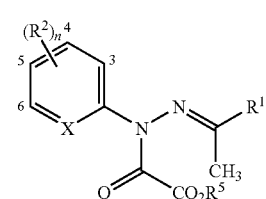

with a base to form a substituted dihydropyrazole having an alkoxide couterion; and when preparing a compound of Formula I wherein $R^3$ is $C_1$-$C_4$ alkyl, $C_2$-$C_4$ alkylcarbonyl or $C_2$-$C_6$ alkoxycarbonyl,
  (2) reacting the substituted dihydopyrazole with an alkylating or acylating agent suitable for substituting an $R^3$ for said alkoxide counterion; and (B) preparing said compound of Formula II by a method comprising (3) treating the compound of Formula I prepared in (A) with acid; to form a substituted pyrazole, and when preparing a compound of Formula II wherein $R^6$ is H, (4) converting the product of (3) to form a compound of Formula II wherein $R^6$ is H.

20. The method of claim 8 where said methyl 1-(1-chloro-2-phenyl)-4,5-dihydro-5-hydroxy-3-(trifluoromethyl)-1H-pyrazole-5-carboxylate is prepared by treating

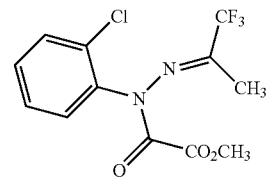

with tetrabutylammonium fluoride hydrate and then acidifying the resulting substituted dihydropyrazole with acetic acid.

* * * * *

UNITED STATES PATENT AND TRADEMARK OFFICE
CERTIFICATE OF CORRECTION

| | |
|---|---|
| PATENT NO. | : 7,622,595 B2 |
| APPLICATION NO. | : 11/352805 |
| DATED | : November 24, 2009 |
| INVENTOR(S) | : Gary David Annis et al. |

It is certified that error appears in the above-identified patent and that said Letters Patent is hereby corrected as shown below:

The unit ""°C." should be replaced with ""°C" in all of the following places

Column 8, lines 16 and 19

Column 10, line 67

Column 11, lines 18, 19, 25, 44 and 51

Column 12, lines 1, 2 and 33

Claim 16 in Column 19, lines 61 and 62

Claim 17 in Column 20, line 5

Claim 18 in Column 20, line 12

Signed and Sealed this
Twenty-sixth Day of February, 2013

Teresa Stanek Rea
*Acting Director of the United States Patent and Trademark Office*